United States Patent [19]

Hoshino et al.

[11] Patent Number: 4,880,852

[45] Date of Patent: Nov. 14, 1989

[54] DEODORIZING POLYOLEFIN RESIN COMPOSITIONS AND FORMED DEODORIZING ARTICLES CONTAINING A MIXTURE OF A ZINC COMPOUND AND A SULFATE OF ALUMINUM

[75] Inventors: Akira Hoshino, Koshigaya; Mikio Saji, Kasukabe; Isamu Yamaguchi, Souka, all of Japan

[73] Assignee: Dainichiseika Color & Chemicals Mfg. Co., Ltd., Tokyo, Japan

[21] Appl. No.: 185,409

[22] Filed: Apr. 25, 1988

Related U.S. Application Data

[62] Division of Ser. No. 928,377, Nov. 10, 1986.

[30] Foreign Application Priority Data

Apr. 7, 1986 [JP] Japan .................................. 61-078181
Apr. 7, 1986 [JP] Japan .................................. 61-078182
Apr. 7, 1986 [JP] Japan .................................. 61-078183
May 13, 1986 [JP] Japan .................................. 61-107543

[51] Int. Cl.$^4$ ........................... C08K 322; C08K 9/12; C11B 9/00; A61K 7/00
[52] U.S. Cl. ..................................... 523/102; 524/423
[58] Field of Search ....................... 523/102; 524/423

[56] References Cited

U.S. PATENT DOCUMENTS 4,735,972 4/1988 Shigematsu et al. ................. 523/102
4,757,099 7/1988 Hoshino et al. ...................... 523/102

*Primary Examiner*—Herbert J. Lilling
*Attorney, Agent, or Firm*—Oblon, Spivak, McClelland, Maier & Neustadt

[57] ABSTRACT

A deodorizing resin composition is composed of 99.9–50 parts by weight of a thermoplastic resin and 0.1–50 parts by weight of a deodorizing ingredient. The deodorizing ingredient is a white or substantially colorless deodorizing agent, which may be preferably be composed of 10–90 parts by weight of a zinc compound and 90–10 parts by weight of an aliphatic polycarboxylic acid or a salt thereof, an aromatic polycarboxylic acid or a salt thereof, an acidic polymer or a salt thereof, or a sulfate of aluminum. A formed deodorizing article can be obtained by forming or molding the deodorizing resin composition into a desired shape. Formed articles of the deodorizing resin composition of this invention can have desired beautiful colors and are adapted to absorb offensive odors.

6 Claims, No Drawings

DEODORIZING POLYOLEFIN RESIN COMPOSITIONS AND FORMED DEODORIZING ARTICLES CONTAINING A MIXTURE OF A ZINC COMPOUND AND A SULFATE OF ALUMINUM

This is a division of application Ser. No. 928,377, filed Nov. 10, 1986.

BACKGROUND OF THE INVENTION (1) Field of the Invention

This invention relates to deodorizing resin compositions and formed deodorizing articles, and more specifically to formed deodorizing articles suitable expecially for use in packaging or wrapping various malodorous articles and the like. The term "formed articles" as used herein should be interpreted in a broad sense so that it embraces therein various formed articles such as films, sheets, molded articles, etc.

(2) Description of the Prior Art

Deodorizers have been being used widely against various offensive odor sources. In order to package various malodorous articles, plastic films, aluminum foils, metal containers, glass containers and the like which do not have air permeability are used primarily.

Packages making use of such conventional packaging or wrapping materials, which do not have air permeability, can prevent emission of offensive odors of contents. Their handling is however inconvenient because offensive odors filling the interiors of the packages come out at once when the packages are opened.

SUMMARY OF THE INVENTION

The present inventors have carried out an extensive investigation with a view toward providing a solution to such drawbacks of conventional techniques as mentioned above. As a result, it has been found that they can be solved by the incorporation of certain specific materials in a thermoplastic resin to be employed upon production of a formed article such as plastic sheet or plastic container since the resulting formed article, for example, packaging material has excellent deodorizing capacity, leading to completion of this invention.

In one aspect of this invention, there is thus provided a deodorizing resin composition comprising 99.9–50 parts by weight of a thermoplastic resin and 0.1–50 parts by weight of a deodorizing ingredient. The deodorizing ingredient is a white or substantially colorless deodorizing agent.

In another aspect of this invention, there is also provided a formed deodorizing article obtained by forming the above-described deodorizing resin composition.

It has been known in the prior art to use a ferrous salt as a deodorizing ingredient of a deodorizer. When such a deodorizing ingredient is used in a form kneaded in a thermoplastic resin or the like, the ferrous salt however undergoes discoloration due to the high processing temperature of the thermoplastic resin. Accordingly, the thermoplastic resin is tinged in a brown color and at the same time, its deodorizing effects are lowered. Moreover, the commercial values of resin articles to be formed from such a resin will lowered significantly. When activated carbon is used on the other hand, the thermoplastic resin is tinged in a black color. Unlike such prior art techniques, a white or substantially colorless zinc compound is employed in lieu of such a ferrous salt or activated carbon in the present invention. On addition, a white or substantially colorless aliphatic polycarboxylic acid or the like is also used in combination with the zinc compound, so that even at high processing temperatures employed upon kneading such deodorizing agents into the thermoplastic resin, the deodorizing agents do not lose their deodorizing effects and undergo little discoloration into brown or black colors. It has also been found that the zinc compound and the aliphatic polycarboxylic acid or the like exhibit synergistic deodorizing effects greater than the sum of their respective deodorizing effects. The deodorizing resin composition of this invention can therefore exhibit sufficient deodorizing effects not only for offensive odor components of the amine type but also for sulfur-containing offensive odor components. In addition, the resultant thermoplastic resin composition is either white or substantially colorless, it can be colored into any desired hue with one or more other colorants.

Formed articles of the deodorizing resin composition of this invention can therefore have desired beautiful colors. When packaging materials of this invention are used for the package of highly malodorous produces, products, articles or the like, for example, fish, processed fish products, various pickled or salted vegetables, various other foods and the like, the packaging materials themselves absorb offensive odors given off from them. It is hence possible to avoid emission of strong offensive odors into the surrounding atmosphere when these packages are opened. For the same reasons, usefulness of packaging materials according to this invention are not limited to foods but they are equally effective in packaging various domestic kitchen refuse, factory refuse and the like.

Besides such packaging materials, the deodorizing resin composition of this invention is also useful as formed deodorizing articles suitable for use at places where unpleasant or offensive odors occur or remain, for example, as raw materials for granular deodorizers, deodorizing wall decorating or finishing materials, deodorizing fibers and textile and other formed deodorizing articles.

The above and other objects, features and advantages of this invention will become apparent from the following description and the appended claims.

DETAILED DESCRIPTION OF THE INVENTION AND PREFERRED EMBODIMENTS

The term "thermoplastic resin" as used herein includes, for example, synthetic or modified thermoplastic resins, for example, polyolefin resins such as polyethylene and polypropylene, polyvinyl chloride, vinylon, polystyrene, polyamides, polyesters, and cellulose acetate, which have conventionally been used in various formed articles, for example, plastic films, plastic sheets, plastic containers, fibers, etc. All of these thermoplastic resins are readily available on the market for use in the present invention. These thermoplatic resins may be in solid forms or in the form of liquid such as paste.

The individual deodorizing agents useful in the practice of this invention are themselves all known compounds. As the zinc compound, any one of various zinc compounds may be employed, for example, an inorganic zinc compound such as zinc oxide, zinc sulfate, zinc chloride, zinc phosphate, zinc nitrate or zinc carbonate, or an organic zinc salt such as zinc acetate, zinc oxalate, zinc citrate, zinc fumarate or zinc formate, with zinc flower (zinc oxide) or zinc carbonate being particularly preferred.

Illustrative examples of the aliphatic polycarboxylic acid useful in the practice of this invention may include di- and tri-carboxylic acids such as oxalic acid, malonic acid, succinic acid, glutaric acid, adipic acid, pimelic acid, fumaric acid, maleic acid, methylmaleic acid, methylfumaric acid, itaconic acid, citraconic acid, mesaconic acid, acetylenic acid, malic acid, methylmalic acid, citric acid, isocitric acid and tartaric acid as well as their salts. In the present invention, citric acid or fumaric acid or its salt is especially preferred.

The term "aromatic carboxylic acid or a salt thereof" as used herein includes, for example, phthalic acid, terephthalic acid, isophthalic acid, trimellitic acid, 1,2,3-benzenetricarboxylic acid, 1,2,3-benzenetricarboxylic acid, pyromellitic acid, benzenehexacarboxylic acid, naphthalenedicarboxylic acid, naphthalenetricarboxylic acid, naphthalenetetracarboxylic acid, diphenyltetracarboxylic acid and azobenzenetetracarboxylic acid, as well as their anhydrides and salts. It is trimellitic acid or its salt that is particularly preferred in the present invention.

The term "acidic polymer" as used herein means a polymer containing sulfonic groups, carboxylic groups, sulfuric ester groups, phosphoric ester groups or phenolic hydroxyl groups in its molecule. It may, for example, include the following polymers.

(a) Polymers containing carboxylic groups:
Polyesters with terminal carboxyl groups, obtained by reacting polycarboxylic acids such as citric acid, tartaric acid and phthalic acid and polyhydric alcohols such as ethylene glycol, 1.4-butanediol and diethylene glycol while using the acids in excess amounts;
Acidic cellulose derivatives modified by various polycarboxylic acids;
Homopolymers of vinyl ether ester monomers and the like or polycarboxylic acids, and random copolymers, block copolymers, graft copolymers and like of the vinyl ether ester monomers and and other general monomers;
Homopolymers of monomers such as acrylic acid and methacrylic acid and random copolymers, block copolymers, graft copolymers and like of the monomers and other general monomers;
Homopolymers of $\alpha,\beta$-unsaturated vinyl monomers such as maleic anhydride and itaconic acid, and random copolymers, block copolymers, graft copolymers and like of the vinyl monomers;

(b) Polymers containing sulfonic groups:
Cellulose derivative such as ethyl cellulose, hydrogenacetate hydrogensulfate phthalate, cellulose hydrogenacetate hydrogensulfate phthalate, ethyl cellulose hydrogensulfobenzoate, sulfonbenzyl cellulose acetate and ethyl sulfoethyl cellulose acetate;
Sulfonic acid modified polymers obtained by modifying polyvinyl alcohol or vinyl alcohol copolymers with sulfonic acid compounds (for example, o-sulfobenzoic acid, sulfopropionic acid, sulfovaleric acid, sulfobenzaldehyde, sulfophthalic acid, etc.); and (c) Polymers containing hydroxyl groups:
Homopolymers of other sulfonic acids or phenolic group containing monomers, and random copolymers, block copolymers, graft copolymers and like of the other sulfonic acids or phenolic group containing monomers;

may mentioned acidic modified products obtained by modifying various polymers with carboxyl carboxyl, sulfonic or phenolic group containing compounds.

Of these, carboxyl-containing polymers are particularly preferred.

The term "sulfate of aluminum" as used herein include aluminum sulfate [$Al_2(SO_4)_3$] and potassium aluminum sulfate [$KAl(SO_4)_3$] with aluminum sulfate being especially preferred.

The principal feature of this invention reside in the use, as a deodorizing ingredient, of at least one compound selected from the group consisting of aliphatic polycarboxylic acids, aromatic carboxylic acids, acidic polymers and sulfates of aluminum in combination with the above-described zinc compound.

It has been known in the prior art to use a ferrous salt or activated carbon as a deodorizing ingredient of a deodorizer. When the ferrous salt is used in a form kneaded in a thermoplastic resin or the like, the ferrous salt however undergoes discoloration because the processing temperature of the thermoplastic resin or the like is high. Hence, the thermoplastic resin or the like is tinged in a brown color and at the same time, its deodorizing effects are lowered. It is also difficult to apply other colors. Moreover, the commercial values of resin articles to be formed from such a resin will lowered significantly. When activated carbon is used in a form kneaded in a thermoplastic resin on the other hand, the thermoplastic resin is tinged in a black color. It was also impossible to apply other colors to the thermoplastic resin.

In the present invention, a white or substantially colorless zinc compound is employed in lieu of such a ferrous salt or activated carbon. In addition, at least one compound selected from the above-described group is also used in combination with the zinc compound, so that even at high processing temperatures employed upon kneading such deodorizing agents into the thermoplastic resin, the deodorizing agents do not lose their deodorizing effects and undergo little discoloration into a brown color and the thermoplastic resin is hence not tinged. It has also been found that the zinc compound and the aliphatic polycarboxylic acid or the like exhibit synergistic deodorizing effects greater than the sum of their respective deodorizing effects. The deodorizing resin composition of this invention can therefore exhibit sufficient deodorizing effects not only for offensive odor components of the amine type but also for sulfur-containing offensive odor components. In addition, the resultant thermoplastic resin composition is not tinged into a brown or black color by the above deodorizing agents and it can therefore be tinged easily into a desired color with one or more other colorants.

In the deodorizing ingredient composed of a zinc compound and an aliphatic polycarboxylic acid or the like such as those described above, their proportions are also important. Supposing the total amount is 100 parts by weight, the zinc compound is used in an amount of 10–90 parts by weight whereas the aliphatic polycarboxylic acid or the like is employed in an amount of 90–10 parts by weight. Such a combination and mixing ratio can best achieve the objects of this invention.

The deodorizing resin composition of this invention requires the above-mentioned combination of the components as essential components. Besides, various additives known conventionally for resins, for example, one or more of colorants, fillers, extender pigments, plasticizers, stabilizers, ultraviolet absorbents and the like may also be incorporated as needed.

The deodorizing resin composition of this invention can be obtained by either simply mixing the above components or melting, kneading and granulating the resultant mixture into pellets. In addition, the deodorizing resin composition of this invention may also be in the form of a master batch which contains the deodorizing ingredient at a high concentration (for example, 10–50 wt. %), so that it may be extended with a plain thermoplastic resin prior to its use.

The deodorizing resin composition of this invention is useful for the production of the formed deodorizing article of this invention.

The formed deodorizing article of this invention is obtained by forming the above-described deodorizing resin composition into any one of various desired shapes, for example, for example, a wrapping material in the form of a plastic film or sheet or in the form of a formed article, e.g., a container of a desired shape obtained by forming the deodorizing resin composition in accordance with any one of various forming or molding methods.

Formation of such films, sheets, containers and the like can be conducted by conventionally-known inflation molding machines, presses, calenders, extrusion molding machines, spinning machines, blow molding machines, injection molding machines, vacuum molding machines and the like under various conventional conditions without need of their modifications. Formed deodorizing articles according this invention can hence be obtained with ease.

This invention will hereinafter be described more specifically by the following Examples, in which all designations of "part or parts" and "%" mean part or parts by weight and wt. % unless otherwise specifically indicated.

EXAMPLE 1

To 99 parts of low-density polyethylene, 1 part of a 10:3 mixture by weight of zinc carbonate and fumaric acid was added. They were mixed in a mixer and then kneaded in a 40 mm extruder (L/D: 28, C.R.: 3.1, Dulmage screw, cylinder temperature: 130° C., screw revolution speed: 70 rpm), thereby a pellet-like deodorizing resin composition of this invention was obtained.

The above deodorizing resin composition was then charged in an inflation molding machine (30 mm extruder, inner diameter of inflation die: 50 mm, cylinder temperature: 140° C., screw revolution speed: 60 rpm) to obtain a polyethylene film having a thickness of about 50 μm. The deodorizing performance of the deodorizing sheet was tested. The following results were obtained.

DEODORIZING TEST ON AMMONIA

The above deodorizing sheet were cut into 50 mm×200 mm sheets. One of the thus-cut sheets was then suspended in a 300-ml Erlenmeyer flask, followed by an addition of 100 ml of 42 ppm aqueous ammonia. The outlet of the flask was sealed with paraffin and the aqueous ammonia was allowed to gasify fully. The flask was thereafter stored at 25° C. and upon an elapse of a predetermined time period, the concentration (ppm) of ammonia in the flask was measured by a Kitagawa's probe. The following results were obtained.

| Lapsed time | 1 day | 2 days | 9 days |
| --- | --- | --- | --- |
| Blank | 25 | 25 | 25 |
| Invention product | 20 | 15 | 10 |
| Comparative Example | 20 | 18 | 15 |

DEODORIZING TEST ON HYDROGEN SULFIDE

One of the above-cut sheets was placed in a 300-ml Erlenmeyer flask, followed by addition of 1 ml of an 800 ppm solution of sodium sulfide in water and 0.1 ml of 1N sulfuric acid. The outlet of the flask was sealed with paraffin and the resulting hydrogen sulfide was allowed to gasify fully. The flask was thereafter stored at 25° C. and upon an elapse of a predetermined time period, the concentration (ppm) of hydrogen sulfide in the flask was measured by a Kitagawa's probe. The following results were obtained.

| Lapsed time | 1 day | 2 days | 9 days |
| --- | --- | --- | --- |
| Blank | 155 | 155 | 155 |
| Invention product | 40 | 3 | trace |
| Comparative Example | 55 | 5 | 1 |

EXAMPLES 2–18

Plastic wrapping films of this invention were separately obtained in the same manner as in Example 1 except that the following ingredients were used. Following the procedure of Example 1, their performance was measured. Results are given below.

EXAMPLE 2

| High-density polyethylene | 95 parts |
| --- | --- |
| 8:2 Mixture of zinc oxide and fumaric acid | 5 parts |

Deodorizing test on ammonia:

| Lapsed time | 1 day | 2 days | 9 days |
| --- | --- | --- | --- |
| Blank | 25 | 25 | 25 |
| Invention product | 20 | 15 | 10 |
| Comparative Example | 20 | 18 | 15 |

Deodorizing test on hydrogen sulfide:

| Lapsed time | 1 day | 2 days | 9 days |
| --- | --- | --- | --- |
| Blank | 155 | 155 | 155 |
| Invention product | 30 | trace | not detected |
| Comparative Example | 55 | 5 | 1 |

EXAMPLE 3

| Polypropylene | 95 parts |
| --- | --- |
| 5:5 Mixture of zinc carbonate and citric acid | 5 parts |

Deodorizing test on ammonia:

| Lapsed time | 1 day | 2 days | 9 days |
| --- | --- | --- | --- |
| Blank | 25 | 25 | 25 |
| Invention product | 20 | 16 | 12 |

-continued

| | | | |
|---|---|---|---|
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 25 | trace | not detected |
| Comparative Example | 55 | 5 | 1 |

EXAMPLE 4

| | |
|---|---|
| Polystyrene | 98 parts |
| 3:7 Mixture of zinc chloride and fumaric acid | 2 parts |

Deodorizing test on ammonia:

| Lapsed time | 1 day | 2 days | 9 days |
|---|---|---|---|
| Blank | 25 | 25 | 25 |
| Invention product | 17 | 13 | 7 |
| Comparative Example | 20 | 18 | 15 |

Deodorizing test on hydrogen sulfide:

| Lapsed time | 1 day | 2 days | 9 days |
|---|---|---|---|
| Blank | 55 | 55 | 55 |
| Invention product | 40 | 3 | trace |
| Comparative Example | 55 | 5 | 1 |

EXAMPLE 5

| | |
|---|---|
| High-density polyethylene | 99 parts |
| 10:3 Mixture of zinc carbonate and trimellitic acid | 5 parts |

Deodorizing test on ammonia:

| Lapsed time | 1 day | 2 days | 9 days |
|---|---|---|---|
| Blank | 25 | 25 | 25 |
| Invention product | 20 | 15 | 12 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 30 | 1 | not detected |
| Comparative Example | 55 | 5 | 1 |

EXAMPLE 6

| | |
|---|---|
| High-density polyethylene | 95 parts |
| 8:2 Mixture of zinc oxide and trimellitic acid | 5 parts |

Deodorizing test on ammonia:

| Lapsed time | 1 day | 2 days | 9 days |
|---|---|---|---|
| Blank | 25 | 25 | 25 |
| Invention product | 20 | 15 | 11 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 30 | not detected | not detected |
| Comparative Example | 55 | 5 | 1 |

EXAMPLE 7

| | |
|---|---|
| Polypropylene | 95 parts |
| 5:5 Mixture of zinc carbonate and trimellitic acid | 5 parts |

Deodorizing test on ammonia:

| Lapsed time | 1 day | 2 days | 9 days |
|---|---|---|---|
| Blank | 25 | 25 | 25 |
| Invention product | 20 | 16 | 11 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 40 | 3 | trace |
| Comparative Example | 55 | 5 | 1 |

EXAMPLE 8

| | |
|---|---|
| Polystyrene | 98 parts |
| 3:7 Mixture of zinc chloride and trimellitic acid | 2 parts |

Deodorizing test on ammonia:

| Lapsed time | 1 day | 2 days | 9 days |
|---|---|---|---|
| Blank | 25 | 25 | 25 |
| Invention product | 17 | 13 | 11 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 45 | 3 | not detected |
| Comparative Example | 55 | 5 | 1 |

EXAMPLE 9

| | |
|---|---|
| High-density polyethylene | 99 parts |
| 10:3 Mixture of zinc carbonate and an acidic polymer ("NEW FRONTIER MI-400P", trade name; product of Dai-ichi Kogyo Seiyaku Co., Ltd., Kyoto, Japan) | 1 parts |

Deodorizing test on ammonia:

| Lapsed time | 1 day | 2 days | 9 days |
|---|---|---|---|
| Blank | 25 | 25 | 25 |
| Invention product | 20 | 15 | 12 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 30 | trace | not detected |

-continued

| | | | |
|---|---|---|---|
| Comparative Example | 55 | 5 | 1 |

EXAMPLE 10

| | |
|---|---|
| High-density polyethylene | 95 parts |
| 8:2 Mixture of zinc oxide and an acidic polymer ("TESKYD MRM43", trade name; product of Hitachi Kasei Polymer Co., Ltd., Tokyo, Japan). | 5 parts |

Deodorizing test on ammonia:

| Lapsed time | 1 day | 2 days | 9 days |
|---|---|---|---|
| Blank | 25 | 25 | 25 |
| Invention product | 20 | 15 | 13 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 30 | trace | not detected |
| Comparative Example | 55 | 5 | 1 |

EXAMPLE 11

| | |
|---|---|
| Polypropylene | 95 parts |
| 5:5 Mixture of zinc carbonate and an acidic polymer ("TESKYD MRA-L", trade name; product of Hitachi Kasei Polymer Co., Ltd., Tokyo, Japan). | 5 parts |

Deodorizing test on ammonia:

| Lapsed time | 1 day | 2 days | 9 days |
|---|---|---|---|
| Blank | 25 | 25 | 25 |
| Invention product | 20 | 16 | 12 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 25 | trace | not detected |
| Comparative Example | 55 | 5 | 1 |

EXAMPLE 12

| | |
|---|---|
| Polystyrene | 98 parts |
| 3:7 Mixture of ferrous sulfide and an acidic polymer ("NEW FRONTIER MI-400P", trade name; prouct of Dai-ichi Kogyo Seiyaku Co., Ltd., Kyoto, Japan) | 2 parts |

Deodorizing test on ammonia:

| Lapsed time | 1 day | 2 days | 9 days |
|---|---|---|---|
| Blank | 25 | 25 | 25 |
| Invention product | 17 | 13 | 10 |
| Comparative Example | 20 | 18 | 15 |

Deodorizing test on hydrogen sulfide:

| Lapsed time | 1 day | 2 days | 9 days |
|---|---|---|---|

-continued

| | | | |
|---|---|---|---|
| Blank | 55 | 55 | 55 |
| Invention product | 40 | 3 | trace |
| Comparative Example | 55 | 5 | 1 |

EXAMPLE 13

| | |
|---|---|
| High-density polyethylene | 95 parts |
| 8:2 Mixture of aluminum sulfate and an acidic polymer ("TESKYD MRM43", trade name; product of Hitachi Kasei Polymer Co., Ltd., Tokyo, Japan). | 5 parts |

Deodorizing test on ammonia:

| Lapsed time | 1 day | 2 days | 9 days |
|---|---|---|---|
| Blank | 25 | 25 | 25 |
| Invention product | 20 | 15 | 12 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 30 | trace | not detected |
| Comparative Example | 55 | 5 | 1 |

EXAMPLE 14

| | |
|---|---|
| Polyethylene | 95 parts |
| 5:3:2 Mixture of zinc carbonate, aluminum sulfate and an acidic polymer ("TESKYD MRA-L", trade name; product of Hitachi Kasei Polymer Co., Ltd., Tokyo, Japan) | 5 parts |

Deodorizing test on ammonia:

| Lapsed time | 1 day | 2 days | 9 days |
|---|---|---|---|
| Blank | 25 | 25 | 25 |
| Invention product | 20 | 16 | 12 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |
| Invention product | 25 | trace | not detected |
| Comparative Example | 55 | 5 | 1 |

EXAMPLE 15

| | |
|---|---|
| High-density polyethylene | 99 parts |
| 10:3 Mixture of zinc carbonate and aluminum sulfate | 1 parts |

Deodorizing test on ammonia:

| Lapsed time | 1 day | 2 days | 9 days |
|---|---|---|---|
| Blank | 25 | 25 | 25 |
| Invention product | 20 | 15 | 11 |
| Comparative Example | 20 | 18 | 15 |

Deodorizing test on hydrogen sulfide:

| Lapsed time | 1 day | 2 days | 9 days |
|---|---|---|---|
| Blank | 155 | 155 | 155 |

| -continued | | | |
|---|---|---|---|
| Invention product | 30 | 1 | not detected |
| Comparative Example | 55 | 5 | 1 |

EXAMPLE 16

| High-density polyethylene | | 95 parts | |
|---|---|---|---|
| 8:2 Mixture of zinc oxide and aluminum sulfate | | 5 parts | |
| Deodorizing test on ammonia: | | | |
| Lapsed time | 1 day | 2 days | 9 days |
| Blank | 25 | 25 | 25 |
| Invention product | 20 | 15 | 12 |
| Comparative Example | 20 | 18 | 15 |
| Deodorizing test on hydrogen sulfide: | | | |
| Lapsed time | 1 day | 2 days | 9 days |
| Blank | 155 | 155 | 155 |
| Invention product | 25 | 1 | not detected |
| Comparative Example | 55 | 5 | 1 |

EXAMPLE 17

| Polyethylene | | 95 parts | |
|---|---|---|---|
| 5:5 Mixture of zinc carbonate and potassium aluminum sulfate | | 5 parts | |
| Deodorizing test on ammonia: | | | |
| Lapsed time | 1 day | 2 days | 9 days |
| Blank | 25 | 25 | 25 |
| Invention product | 18 | 13 | 10 |
| Comparative Example | 20 | 18 | 15 |
| Deodorizing test on hydrogen sulfide: | | | |
| Lapsed time | 1 day | 2 days | 9 days |
| Blank | 155 | 155 | 155 |
| Invention product | 35 | 2 | not detected |
| Comparative Example | 55 | 5 | 1 |

EXAMPLE 18

| Polystyrene | | 98 parts | |
|---|---|---|---|
| 3:7 Mixture of zinc chloride and aluminum sulfate | | 2 parts | |
| Deodorizing test on ammonia: | | | |
| Lapsed time | 1 day | 2 days | 9 days |
| Blank | 25 | 25 | 25 |
| Invention product | 17 | 13 | 10 |
| Comparative Example | 20 | 18 | 15 |
| Deodorizing test on hydrogen sulfide: | | | |
| Lapsed time | 1 day | 2 days | 9 days |
| Blank | 155 | 155 | 155 |
| Invention product | 30 | 1 | not detected |
| Comparative Example | 55 | 5 | 1 |

In each of the above Examples 1-18, a film free of any deodorizing ingredient was used as the blank while a film making use of ferrous sulfate alone was employed in the Comparative Example.

Furthermore, the comparative products were all stained in brown colors while those produced respectively from the invention products were not stained practically.

In addition, bags were produced respectively from the films employed as the blanks, invention products and comparative products in Examples 1-18. Thawed small fish was placed within the bags. The bags were left over and were then opened three days later. Little offensive odors were felt in the bags produced from the films of this invention, whereas strong offensive odors were emitted from the bags made of the blanks. Furthermore, the comparative products were all stained deeply in brown colors while those produced respectively from the invention products were not stained practically.

EXAMPLE 19

Added to 80 parts of high-density polyethylene were 20 parts of a 10:4 mixture by weight of zinc oxide and fumaric acid. The procedure of Example 1 was then followed to obtain a deodorizing resin composition of this invention which contained the deodorizing ingredient at a concentration of 20%.

The deodorizing resin composition was extended with plain high-density polyethylene to a total volume 20 times the original. The resulting resin composition was then molded into a bottle-like molded article having a wall thickness of 1 mm, a diameter of 60 mm and a height of 170 mm by means of a blow molding machine (45 mm screw, screw revolution speed: 30 rpm, cylinder temperature: 200° C.). Partially tainted meat was hermetically sealed within the molded article. After allowing the molded article to stand for 3 days, the offensive odor was remarkably weaker compared with that emitted from a molded article similar to the above molded article except for the exclusion of the deodorizing ingredient.

The following deodorizing ingredients were used instead of the above-described deodorizing ingredients. Similar results were obtained.

(1) A 10:4 mixture by weight of zinc oxide and trimellitic anhydride.

(2) A 10:4 mixture by weight of zinc oxide and an acidic polymer ("NEW FRONTIER MI-400P", trade name; product of Dai-ichi Kogyo Seiyaku Co., Ltd., Kyoto, Japan)

(3) A 10:4 mixture by weight of zinc oxide and potassium aluminum sulfate.

EXAMPLE 20

Seventy parts of polypropylene and 30 parts of a deodorizing ingredient (a 10:3 mixture of zinc acetate and fumaric acid) were mixed together. They were mixed for 2 minutes at 1,500 rpm in a Henschel mixer and then kneaded in a 40-mm extruder (L/D: 28; C.R.: 3.1; Dulmage screw; cylinder temperature: 200°-215° C.; screw revolution speed: 90 rpm), thereby obtaining pellet-like deodorizing resin composition of this invention. It was extended to a natural resin to a total volume 10 times it original volume. The thus-extended resin was spun at 200°-215° C. through a spinning machine, followed by stretching at a draw ratio of 3 into fibers of 15 denier. The deodorizing performance of the deodorizing fibers was tested. The following results were obtained.

DEODORIZING TEST ON AMMONIA

One gram of the above deodorizing fibers was placed in a 300-ml Erlenmeyer flask, followed by an addition of 10 μl of 28% aqueous ammonia. The outlet of the flask was sealed with paraffin and the aqueous ammonia was allowed to gasify fully. The flask was thereafter stored at 25° C. and upon an elapse of a predetermined time period, the concentration (ppm) of ammonia in the flask was measured by a Kitagawa's probe. The following results were obtained.

| Lapsed time | 5 minutes | 30 minutes | 120 minutes |
| --- | --- | --- | --- |
| Blank | 4000 | 4000 | 4000 |
| Invention product | 2500 | 850 | 300 |
| Comparative Example | 3000 | 1000 | 500 |

DEODORIZING TEST ON HYDROGEN SULFIDE

One gram of the above deodorizing fibers was placed in a 300-ml Erlenmeyer flask, followed by addition of 1 ml of an 800 ppm solution of sodium sulfide in water and 0.1 ml of 1N sulfuric acid. The outlet of the flask was sealed with paraffin and the resulting hydrogen sulfide was allowed to gasify fully. The flask was thereafter stored at 25° C. and upon an elapse of a predetermined time period, the concentration (ppm) of hydrogen sulfide in the flask was measured by a Kitagawa's probe. The following results were obtained.

| Lapsed time | 1 day | 2 days | 9 days |
| --- | --- | --- | --- |
| Blank | 170 | 170 | 170 |
| Invention product | trace | not detected | not detected |
| Comparative Example | 55 | 3 | 1 |

The above procedure was repeated except for the use of the following deodorizing ingredients instead of the above-described deodorizing ingredient. The following results were obtained.

(1) A 10:3 mixture by weight of zinc acetate and anhydrous sodium trimellitate.

| | Deodorizing test on ammonia: | | |
| --- | --- | --- | --- |
| Lapsed time | 5 minutes | 30 minutes | 120 minutes |
| Blank | 4000 | 4000 | 4000 |
| Invention product | 2500 | 900 | 400 |
| Comparative Example | 3000 | 1000 | 500 |
| | Deodorizing test on hydrogen sulfide: | | |
| Lapsed time | 1 day | 2 days | 9 days |
| Blank | 170 | 170 | 170 |
| Invention product | trace | not detected | not detected |
| Comparative Example | 55 | 3 | 1 |

(2) A 10:3 mixture by weight of zinc oxide and an acidic polyer ("TESKYD MRA-L", trade name; product of Hitachi Kasei Polymer Co., Ltd., Tokyo, Japan)

| | Deodorizing test on ammonia: | | |
| --- | --- | --- | --- |
| Lapsed time | 5 minutes | 30 minutes | 120 minutes |
| Blank | 4000 | 4000 | 4000 |
| Invention product | 2500 | 850 | 300 |
| Comparative Example | 3000 | 1000 | 500 |
| | Deodorizing test on hydrogen sulfide: | | |
| Lapsed time | 1 day | 2 days | 9 days |
| Blank | 170 | 170 | 170 |
| Invention product | trace | not detected | not detected |
| Comparative Example | 5 | 3 | 1 |

(3) A 10:3 mixture by weight of zinc acetate and potassium aluminum sulfate.

| | Deodorizing test on ammonia: | | |
| --- | --- | --- | --- |
| Lapsed time | 5 minutes | 30 minutes | 120 minutes |
| Blank | 4000 | 4000 | 4000 |
| Invention product | 2500 | 850 | 400 |
| Comparative Example | 3000 | 1000 | 500 |
| | Deodorizing test on hydrogen sulfide: | | |
| Lapsed time | 1 day | 2 days | 9 days |
| Blank | 170 | 170 | 170 |
| Invention product | trace | not detected | not detected |
| Comparative Example | 5 | 3 | 1 |

Note
In each of the above tests the blank was fibers not added with any deodorizing ingredient, while ferrous sulfate was used solely in the Comparative Example.
The films of the Comparative Examples were stained in brown colors while the invention products were not stained practically.

EXAMPLE 21

Thoroughly mixed into a plastisol were 50 parts of a PVC paste resin ("SUMILIT PXN", trade name; product of Sumitomo Chemical Co., Ltd., Osaka, Japan), 20 parts of dioctyl phthalate, 4 parts of a plasticizer of the lactic acid ester type ("C.L.P.", trade name; product of Daihachi Chemical Industry Co., Ltd., Osaka, Japan), 1 part of cadmium-barium base stabilizer, 20 parts of calcium carbonate, 5 parts of zinc oxide, and 20 parts of a mixture which consisted of 20 parts by weight of potassium aluminum sulfate, 15 parts by weight of citric acid and 5 parts by weight of sodium citrate. The plastisol was then coated on one side of a flame-retarded paper sheet to a thickness of 0.2 mm, followed by its gelation at 140° C. for 60 seconds. The thus-coated surface was thereafter printed and embossed to provide a deodorizing PVC sheet material of this invention.

The above deodorizing PVC sheet material of this invention was then cut into 50 mm×200 mm sheets. Two sheets were then adhered with their uncoated surfaces inside so as to avoid influence of the uncoated surfaces. The thus-adhered sheets were placed in a 300-ml Erlenmeyer flask, followed by an addition of 10 μl of 28% aqueous ammonia. The flask was hermetically sealed to gasify the ammonia fully. At 25° C., ammonia gas was detected periodically by means of a Kitagawa's probe. The following deodorizing effects were obtained (unit: ppm).

| Lapsed time | 5 minutes | 30 minutes | 120 minutes |
|---|---|---|---|
| Blank | 4000 | 4000 | 4000 |
| Invention product | 2500 | 700 | 100 |

Note
The blank was the same PVC sheet material as the invention product except for the exclusion of the deodorizing ingredient.

Having now fully described the invention, it will be apparent to one of ordinary skill in the art that many changes and modifications can be made thereto without departing from the spirit or scope of the invention as set forth herein.

We claim:

1. A resin composition, comprising: 99.9–50 parts by weight of a thermoplastic polyolefin resin and 0.1–50 parts by weight of a combination of a zinc compound and a sulfate of aluminum, which combination functions as a deodorizing ingredient.

2. The resin composition as claimed in claim 1, wherein the deodorizing agent is composed of 10–90 parts by weight of a zinc compound and 90–10 parts by weight of a sulfate of aluminum.

3. The resin composition as claimed in claim 2, wherein the sulfate of aluminum is aluminum sulfate or potassium aluminum sulfate.

4. A shaped resin article obtained by shaping a resin composition comprising 99.9–50 parts by weight of a thermoplastic polyolefin resin and 0.1–50 parts by weight of a combination of a zinc compound and a sulfate of aluminum, which combination functions as a deodorizing ingredient.

5. The shaped resin article as claimed in claim 1, wherein the deodorizing agent is composed of 10–90 parts by weight of a zinc compound and 90–10 parts by weight of a sulfate of aluminum.

6. The shaped resin article as claimed in claim 5, wherein the sulfate of aluminum is aluminum sulfate or potassium aluminum sulfate.

* * * * *